United States Patent [19]

Koshikawa et al.

[11] Patent Number: 5,181,545
[45] Date of Patent: Jan. 26, 1993

[54] ENDOSCOPE AND JIG FOR PROCESSING SIGNAL CONDUCTORS OF ENDOSCOPE

[75] Inventors: Nobuo Koshikawa, Arakawa; Masahiro Inoue, Shinagawa, both of Japan

[73] Assignee: Kabushiki Kaisha Machida Seisakusho, Tokyo, Japan

[21] Appl. No.: 641,647

[22] Filed: Jan. 15, 1991

Related U.S. Application Data

[62] Division of Ser. No. 530,406, May 30, 1990, Pat. No. 5,003,964.

[30] Foreign Application Priority Data

Jun. 15, 1989 [JP] Japan ................................ 1-69053

[51] Int. Cl.⁵ .............................................. B21F 1/00
[52] U.S. Cl. .................................................. 140/92.1
[58] Field of Search ...................... 72/71 R, 92.1, 106, 72/123

[56] References Cited

U.S. PATENT DOCUMENTS 1,881,659 10/1932 Kellems .............................. 140/92.1
2,902,059 9/1959 Fiore et al. ......................... 140/92.1

Primary Examiner—Lowell A. Larson
Attorney, Agent, or Firm—Fish & Richardson

[57] ABSTRACT

An endoscope includes an electric device attached to a rigid portion provided at a distal end of the endoscope, and signal conductors extending from the electric device. The signal conductors are bent at a bending portion of the endoscope so as to reduce a bending resistance of the bending portion. Each signal conductor has an intersecting portion extending in a direction intersecting the longitudinal direction of the bending portion. A jig for processing or bending the signal conductors includes a plurality of pairs of first and second engagement portions provided on each of opposite sides of the jig. The first engagement portions as well as the second engagement portions arre arranged in a row, and spaced from one another in the longitudinal direction of the jig. Each pair of first and second engagement portions are disposed in a straight line intersecting the longitudinal direction of the jig.

5 Claims, 3 Drawing Sheets

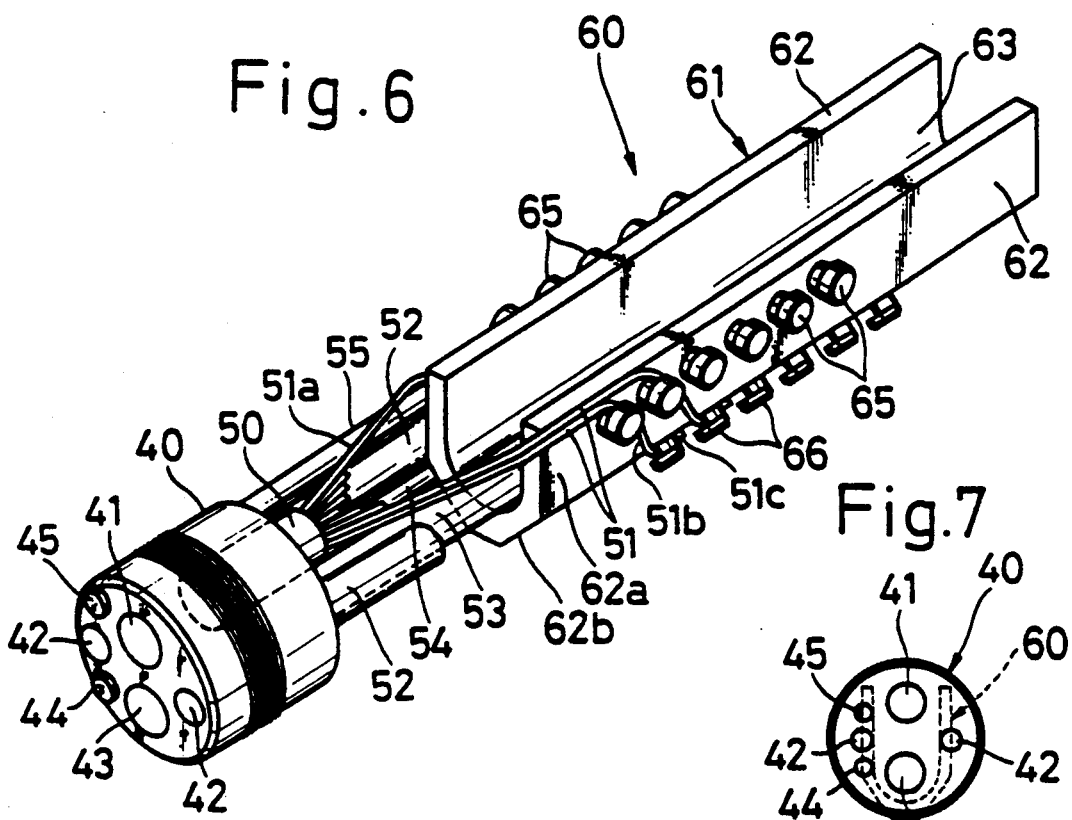
Fig. 6
Fig. 7
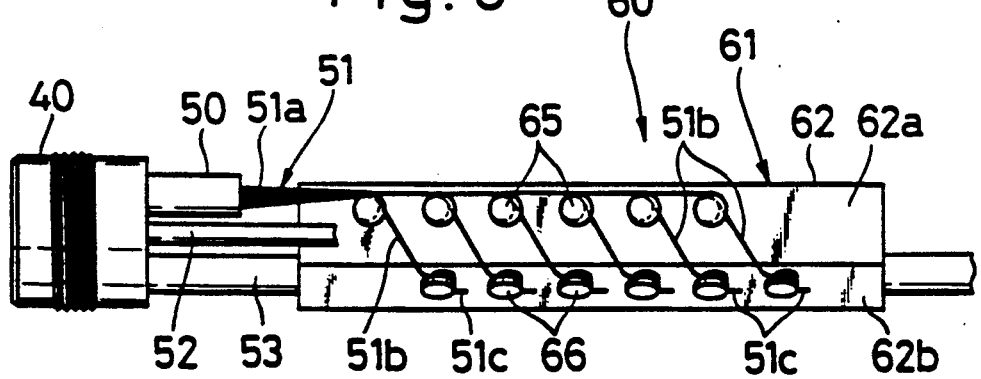
Fig. 8
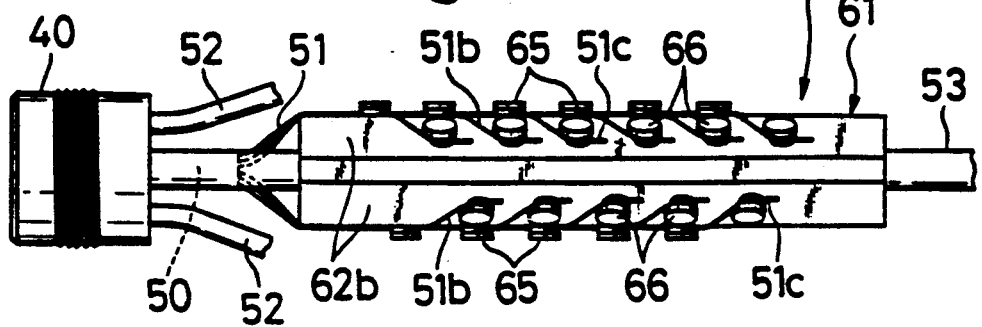
Fig. 9

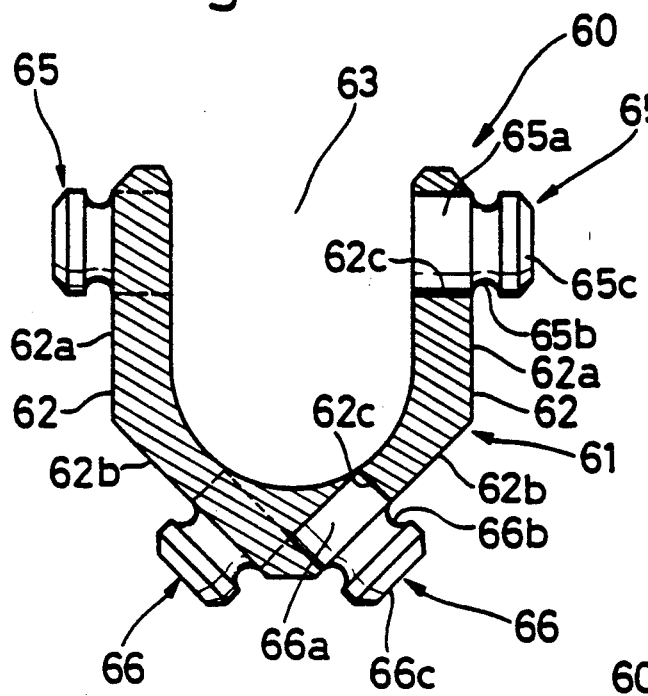
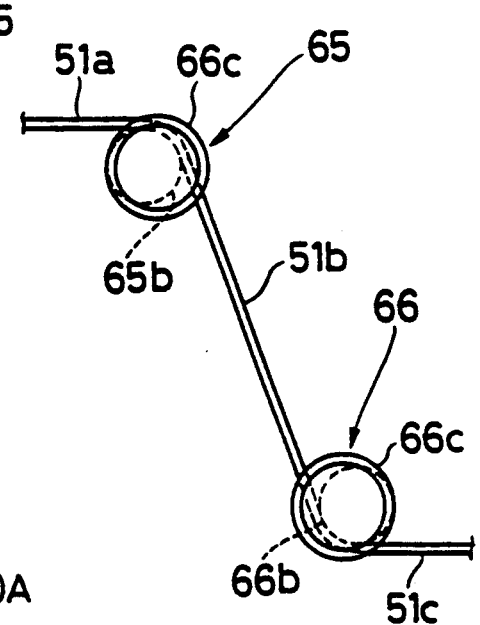
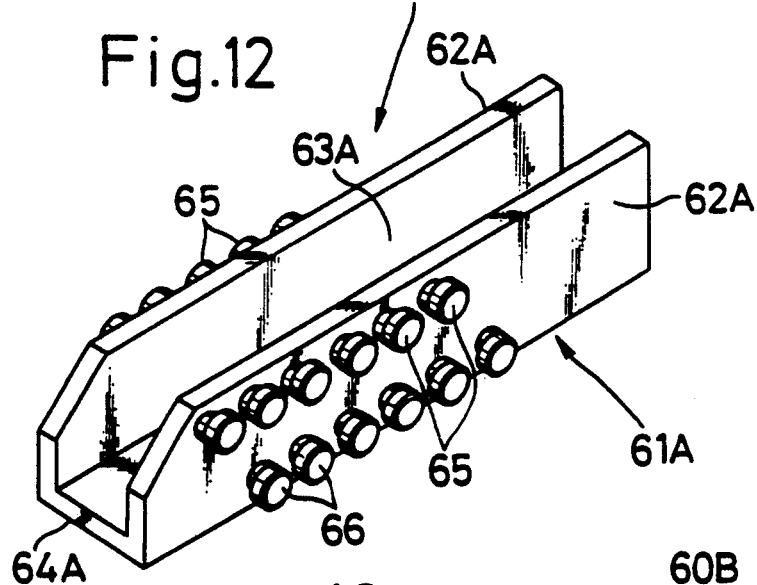
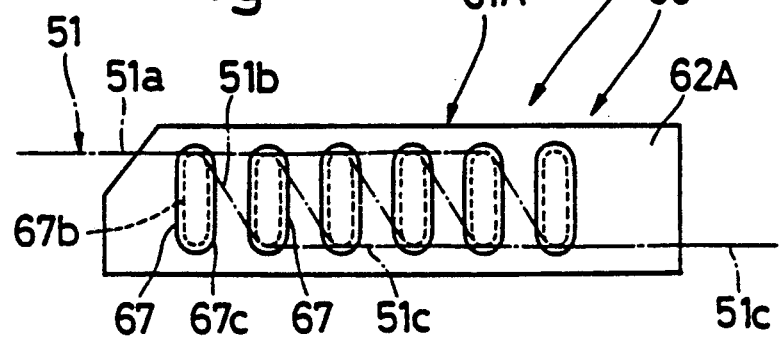

ENDOSCOPE AND JIG FOR PROCESSING SIGNAL CONDUCTORS OF ENDOSCOPE

This application is a division of U.S. application Ser. No. 07/530,406, filed May 30, 1990, now U.S. Pat. No. 5,003,964 granted Apr. 2, 1991.

BACKGROUND OF THE INVENTION

This invention relates to an endoscope having signal conductors and also to a jig for processing such signal conductors.

An endoscope of the type connectable to a television system is already known, for example, from Japanese Laid-Open (Kokai) Patent Application Nos. 90544/84, 50546/86, 267715/87 and 21618/88. Such an endoscope, like other types of endoscopes, comprises a hollow body, a flexible hollow insertion portion extending from the front end of the hollow body, a flexible hollow bending portion extending from the distal end of the insertion portion, and a rigid portion provided at the distal end of the bending portion. The bending portion is remotely manipulated to be bent via operating wires by a manipulating member mounted on the body.

In the endoscope of the above type connectable to a television system, an image sensor (electric device) is attached to the rigid portion, and one ends of signal conductors are connected to the image sensor. A bundle of such signal conductors are passed through the bending portion, the insertion portion and the body, and are connected at the other ends to the television system outside of the body. A bundle of optical fibers for transmitting illumination light, a guide tube for guiding a forceps, and etc., are also passed through the insertion portion and the bending portion.

In the above endoscope of the type described, the bending rigidities of the signal conductors constitute one factor of the overall bending resistance offered by the bending portion when the bending portion is bent. Since the signal conductors are provided in the form of a bundle, they have contributed to an increased bending resistance of the bending portion.

When the bending portion of the above endoscope is bent in a certain direction, the bundle of signal conductors are disposed inwardly of the longitudinal axis (center line) of the bending portion. In this case, the bundle of signal conductors are required to become shorter than when the bending portion is straight Actually, however, the signal conductor bundle is not changed in length, and therefore is subjected to a compressive force, so that the bundle tends to bulge outwardly of the longitudinal axis of the bending portion. On the other hand, the elongated component parts (e.g., the above guide tube) disposed outwardly of the longitudinal axis of the bending portion is required to become longer than when the bending portion is straight. Actually, however, the guide tube is not changed in length, and therefore is subjected to tension, so that the guide tube is displaced inwardly of the longitudinal axis of the bending portion. As a result, the signal conductor bundle and the guide tube are brought into contact with each other, and interfere with each other, thus offering a resistance to the displacement or movement of each of the bundle and the guide tube. This increases the bending resistance of the bending portion.

When the bending portion is bent in a direction opposite to the above-mentioned direction, the signal conductor bundle is subjected to tension and is displaced inwardly of the longitudinal axis of the bending portion whereas the guide tube is subjected to a compressive force and tends to bulge outwardly of the longitudinal axis of the bending portion. As a result, they interfere with each other as in the above case, thus increasing the bending resistance of the bending portion.

When the bending of the bending portion continues with the signal conductor bundle and the guide tube held against each other, part of each of the two is displaced in a direction perpendicular to the direction of bending of the bending portion, and in some cases the bundle and the guide tube are disposed in respective positions which are reverse to those at the time when the bending portion is straight. In this case, however, the bending portion is twisted while being bent, and fails to be bent in a desired direction.

Further, when the signal conductor bundle and the guide tube are held in contact with each other, an axial force (i.e., tension or a compressive force) acts on the signal conductors, and this force is transmitted to the joint between the image sensor and each signal conductor which joint is formed, for example, by soldering. As a result, there is a possibility that this joint may be damaged or broken.

There is also known an endoscope of the type in which signal conductors are not positively arranged in the form of a bundle but are merely passed straight through a bending portion and an insertion portion. With this construction, however, most of the above problems are not overcome.

SUMMARY OF THE INVENTION

It is therefore a first object of this invention to provide an endoscope which is excellent in durability, and has a bending portion which can be bent with a small manipulating force.

A second object of the invention is to provide a jig capable of efficiently bending or processing signal conductors of the endoscope into a required form In order to achieve the first object, according to one aspect of the invention, there is provided an endoscope comprising:

(a) a hollow body having a remotely-manipulating means;

(b) a hollow insertion portion extending from the body;

(c) a hollow bending portion extending from a distal end of the insertion portion, the bending portion being bendable by manipulating the remotely-manipulating means;

(d) a rigid portion mounted on a distal end of the bending portion;

(e) an elongated component part extending from the rigid portion toward the body through the bending portion and the insertion portion;

(f) an electric device attached to the rigid portion; and (g) signal conductors connected at one ends to the electric device and extending therefrom toward the body through the bending portion and the insertion portion, each of the signal conductors being bent at the bending portion and having an intersecting portion extending in a direction intersecting a longitudinal direction of the bending portion.

In order to achieve the second object, according to another aspect of the invention, there is provided a jig for processing signal conductors extending from an electric device attached to a rigid portion provided at a distal end of an endoscope, comprising:

(a) an elongated base; and (b) a plurality of pairs of first and second engagement portions provided on each of opposite sides of the base, the pairs of first and second engagement portions being spaced from each other in a direction intersecting a longitudinal direction of the base, the first engagement portions being arranged substantially in a row and spaced from one another in the longitudinal direction of the base, and the second engagement portions being arranged substantially in a row and spaced from each other in the longitudinal direction of the base;

(c) the signal conductors extending from the electric device being adapted to be divided into two groups which are disposed respectively adjacent to the opposite sides of the base, each of the signal conductors being engaged with a respective one of the pairs of the first and second engagement portions, the signal conductor being engaged with the corresponding first engagement portion to be directed toward the corresponding second engagement portion, and further engaged with the corresponding second engagement portion to extend in the longitudinal direction of the base.

BRIEF DESCRIPTION OF THE DRAWINGS

FIG. 6 is a perspective view of a jig of the present invention, showing a process of bending the signal conductors;

FIG. 7 is a front-elevational view of the jig;

FIG. 8 is a side-elevational view of the jig;

FIG. 9 is a bottom view of the jig;

FIG. 10 is a transverse cross-sectional view of the jig;

FIG. 11 is a side-elevational view showing one pair of projections of the jig with which the signal conductor is engaged for bending purposes;

FIG. 12 is a perspective view of a modified jig; and

FIG. 13 is a side-elevational view of another modified jig.

DESCRIPTION OF THE PREFERRED EMBODIMENTS OF THE INVENTION

One preferred embodiment of an endoscope of the invention will now be described with reference to FIGS. 1 to 5.

Figure 1:
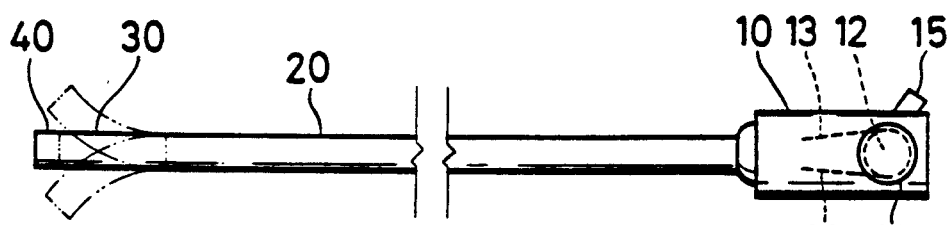
FIG. 1 is a schematic view of an endoscope provided in accordance with the present invention.

The endoscope shown in FIG. 1 comprises a hollow body 10, an insertion portion 20 extending from the front end of the body 10, a bending portion 30 extending from the distal end of the insertion portion 20, a rigid portion 40 mounted on the distal end of the bending portion 30. Each of the insertion portion 20 and the bending portion 30 has a hollow, tubular shape, and is flexible so as to be bent.

A manipulating dial 11 for remotely controlling or manipulating the bending portion 30 is mounted on the body 10. The manipulating dial 11 is connected to a pulley 12 via a shaft (not shown) extending through the wall of the body 10. The pulley 12 is mounted within the body 10, and two operating wires 13 and 14 are fixedly secured at their one ends to the peripheral surface of the pulley 12. The two operating wires 13 and 14 extend forwardly from the upper and lower portions of the pulley 12, respectively, and are fixedly connected at their distal ends to the rigid portion 40. When the manipulating dial 11 is rotated in a clockwise direction (FIG. 1), the upper operating wire 13 is pulled, so that the bending portion 30 is bent upwardly. In contrast, when the manipulating dial 11 is rotated in a counterclockwise direction, the lower operating wire 14 is pulled, so that the bending portion 30 is bent downwardly.

The body 10 has an inlet port 15 for introducing an elongated forceps, and two cables (not shown) are fixedly connected at their one ends to the body 10. An optical connector (not shown) connectable to a light source device is mounted on the other end of one of the two cables. An electrical connector connectable to a television system is mounted on the other end of the other cable.

Figure 2:
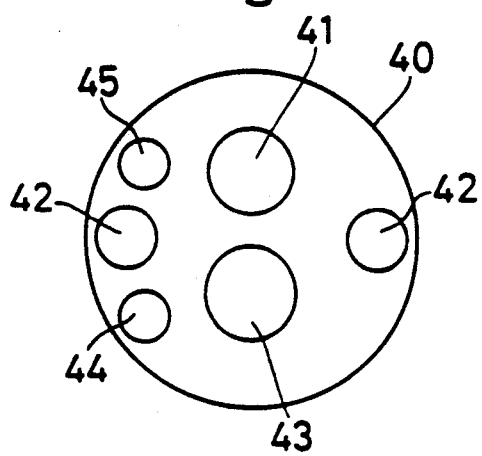
FIG. 2 is a view showing a distal end of the endoscope.

As shown in FIG. 2, an inspection window 41, a pair of illumination windows 42 and 42 and a forceps outlet port 43 are formed in the distal end face of the rigid portion 40, and a water nozzle 44 and an air nozzle 45 are mounted on the distal end face of the rigid portion 40. The inspection window 41 is displaced upwardly from the axis (center line) of the rigid portion 40, and the forceps outlet port 43 is displaced downwardly from the axis of the rigid portion 40. The pair of illumination windows 42 and 42 are disposed on the right and left sides of the axis of the rigid portion 40, respectively. The water nozzle 44 and the air nozzle 45 are disposed on the left side of the axis of the rigid portion 40.

Illumination light fed from the light source device is transmitted to the pair of illumination windows 42 and 42 via a pair of optical fiber bundles 52 and 52. The optical fiber bundles 52 are passed through the above optical connector, the one cable, the body 10, the insertion portion 20 and the bending portion 30.

Figure 3:
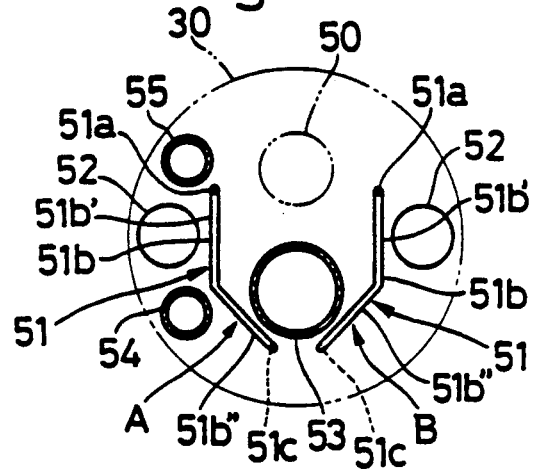
FIG. 3 is a transverse cross-sectional view of a bending portion of the endoscope.
Figure 4:
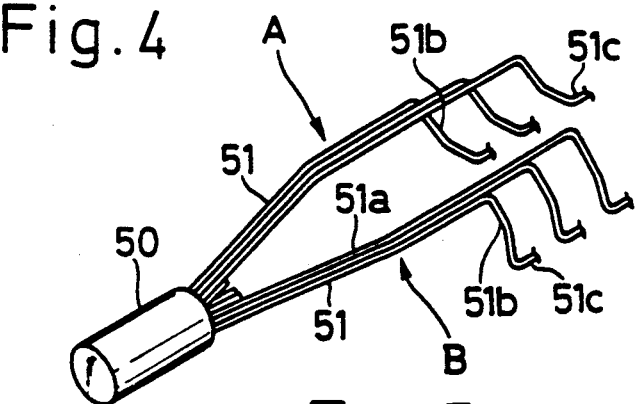
FIG. 4 is a perspective view of signal conductors extending from an image sensor.
Figure 5:
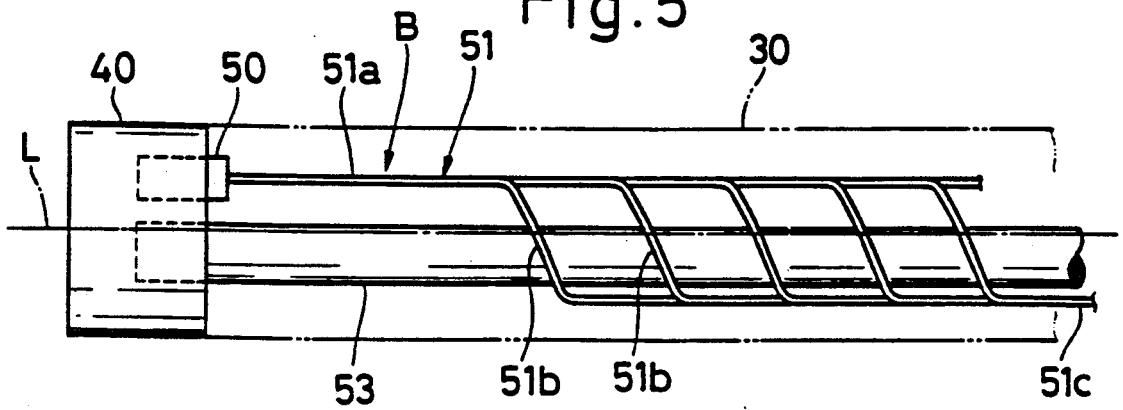
FIG. 5 is a schematic side-elevational view showing the internal structure of the bending portion.

The forceps outlet port 43 is connected to the forceps inlet port 15, provided on the body 10, via a guide tube 53 (see FIGS. 3 and 5). The guide tube 53 is passed through the bending portion 30, the insertion portion 20 and the body 10. The elongated forceps (not shown) is inserted into the forceps inlet port 15, and is passed through the guide tube 53, and its distal end is projected from the forceps outlet port 43. The distal end of the forceps projected from the forceps outlet port 43 is remotely controlled via its proximal end projected from the forceps inlet port 15, so that the distal end of the forceps effects the required operation.

The water nozzle 44 and the air nozzle 45 are connected via water feed tube 54 and air feed tube 55 (FIG. 3) respectively to a pressurized water source and a pressurized air source disposed outside of the body 10. The tubes 54 and 55 are passed through the bending portion 30, the insertion portion 20 and the body 10. With this construction, water and air are injected respectively from the water nozzle 44 and the air nozzle 45 toward the inspection window 41 so as to remove dirt on the inspection window 41.

The optical fiber bundles 52, the guide tube 53, the water feed tube 54 and the air feed tube 55 are connected at their distal ends to the rigid portion 40. An image sensor (electric device) 50 such as CCD is mounted on the rigid portion 40. The image sensor 50 is optically connected to the inspection window 41 via an ocular lens system (not shown). A plurality of (for example, eleven) signal conductors 51 each in the form of a shield electric wire are fixedly connected at their one ends to a connector terminal, provided at the rear end of the image sensor, by soldering or the like. The signal conductors 51 extend from the image sensor 50, and are passed through the bending portion 30, the insertion portion 20, the body 10 and the other cable mentioned above, and are connected at the other ends thereof to the television system via the electrical connector.

As shown in FIG. 3, in the bending portion 30, the optical fiber bundles 52, the guide tube 53, the water feed tube 54 and the air feed tube 55 are disposed substantially in registry with the illumination windows 42, the forceps outlet port 43, the water nozzle 44 and the air nozzle 45, respectively.

In the bending portion 30, the signal conductors 51 are not disposed in registry with the image sensor 50. The signal conductors 51 are divided into two groups (i.e., generally two halves) disposed respectively on the right and left sides of the longitudinal axis L of the bending portion 30, the two groups being spaced from each other in a direction perpendicular to the direction of bending of the bending portion 30. For example, the eleven signal conductors 51 are divided into two groups A and B, and the group A consists of five signal conductors 51 whereas the group B consists of six signal conductors 51. The group A is disposed on the left side (FIG. 3), and the group B is disposed on the right side.

Each of the signal conductors 51 is bent at the bending portion 30, and has a front portion 51a extending rearwardly from the image sensor 50 substantially in the longitudinal direction of the bending potion 30, an intersecting portion 51b extending from the rear end of the front portion 51a in downwardly inclined and intersecting relation to the longitudinal direction of the bending portion 30, and a rear portion 51c extending rearwardly from the rear end of the intersecting portion 51b substantially in the longitudinal direction of the bending portion 30. The intersecting portion 51b is inclined with respect to the longitudinal axis (center line) L of the bending portion 30. The intersection portion 51b is connected at its front end to the front portion 51a at an obtuse angle, and also is connected at its rear end to the rear portion 51c at an obtuse angle. As shown in FIG. 3, each intersecting portion 51b is bent intermediate the opposite ends thereof to provide an upper section 51b' and a lower section 51b''. The upper section 51b' is substantially parallel to the plane along which the bending portion 30 can be bent, and the lower section 51b'' is inclined with respect to this plane.

In each of the groups A and B, the front portions 51a of the signal conductors 51 are disposed in contiguous relation to one another, and the rear portions 51c are also disposed in contiguous relation to one another. The front portions 51a are disposed on the upper side of the longitudinal axis L of the bending portion 30, and the rear portions 51c are disposed on the lower side of the longitudinal axis L. The intersecting portions 51b are spaced from one another at substantially equal intervals in the longitudinal direction of the bending portion 30.

As shown in FIG. 3, the intersecting portions 51b of the signal conductors 51 of the group A and the intersecting portions 51b of the signal conductors 51 of the group B are spaced from each other diametrically of the bending portion 30, that is, disposed respectively on the left and right sides of the longitudinal axis L of the bending portion 30. The guide tube 53 is disposed between the intersecting portions 51b of the group A and the intersecting portions 51b of the group B. One optical fiber bundle 52, the water feed tube 54 and the air feed tube 55 are disposed on the left side of the intersecting portions 51b of the signal conductors 51 of the group A, and the other optical fiber bundle 52 is disposed on the right side of the intersecting portions 51b of the signal conductors 51 of the group B.

In the endoscope of the above construction, that portion of each signal conductor 51 received in the bending portion 30 is beforehand bent into the above configuration, and therefore the bending resistance offered by the bending portion 30 when bending the bending portion 30 can be reduced. The reason for this will now be described. In connection with the bending of the bending portion 30, when each signal conductor 51 is required to be axially expanded and is subjected to tension, the angle between the intersecting portion 51b and the front portion 51a as well as the angle between the intersecting portion 51b and the rear portion 51c is increased. As a result, the signal conductor 51 is expanded in the direction of the longitudinal axis L of the bending portion 30. In contrast, when each signal conductor 51 is required to be contracted and is subjected to a compressive force, the angle between the intersecting portion 51b and the front portion 51a as well as the angle between the intersecting portion 51b and the rear portion 51c is decreased. As a result, the signal conductor 51 is contracted in the direction of the longitudinal axis L of the bending portion 30. Therefore, during the bending of the bending portion 30, the signal conductors 51 will not engage the other component parts, received in the bending portion 30, with a large force, and hence the bending resistance of the bending portion 30 can be reduced.

When the bending portion 30 is bent upwardly, the front portion 51a of each signal conductor 51 is disposed inwardly of the longitudinal axis L of the bending portion 30 whereas the rear portion 51c is disposed outwardly of the longitudinal axis L. In this case, the front portion 51a is required to be contracted, and the rear portion 51c is required to be expanded. Therefore, since the required amount of contraction of the front portion 51a and the required amount of expansion of the rear portion 51c cancel each other, the required amount of change of the length of each signal conductor 51 over the entire length of the bending portion 30 is small. In contrast, when the bending portion 30 is bent downwardly, the required amount of expansion of the front portion 51a and the required amount of contraction of the rear portion 51c cancel each other. The intersecting portion 51b of each signal conductor 51 is merely displaced slightly along the longitudinal axis L. As a result, the amounts of radial displacement of the front portion 51a and the rear portion 51c can be kept to small levels. Therefore, the resistance produced by interference of the signal conductors 51 with the other component parts received in the bending portion 30 can be reduced. This also serves to reduce the bending resistance of the bending portion 30.

The signal conductors 51 are arranged in a dispersed condition. Namely, the signal conductors 51 are divided into the two groups A and B, and in addition the intersecting portions 51b of the signal conductors 51 of each group are spaced from one another in the longitudinal direction of the bending portion 30. Therefore, the bending resistance of the bending portion 30 can be lower as compared with the case where the signal conductors are combined into a bundle. Further, the distribution of the bending rigidity of the bending portion 30 due to the signal conductors 51 can be uniform, and therefore the bending portion 30 can be bent without being twisted.

As described above, the signal conductors 51 are divided into the right and left groups, and the guide tube 53 is interposed therebetween. Therefore, the signal conductors 51 and the guide tube 53 will not interfere with each other when bending the bending portion 30 upwardly and downwardly. This further reduces the bending resistance of the bending portion 30, and prevents the twisting of the bending portion 30 when bending the bending portion 30.

Further, since the axial compressive force and tension, applied to the signal conductors 51 when bending the bending portion 30, can be markedly reduced, the joint between the signal conductors 51 and the image sensor 50 is prevented from being damaged or broken, thereby enhancing the durability of the endoscope.

The endoscope according to the present invention is not restricted to the above embodiment, and various modifications can be made. For example, the bending portion 30 can be designed to be bent not only in upward and downward directions but also in right and left directions.

With respect to the electric device attached to the rigid portion of the endoscope, the image sensor may be replaced by an ultrasonic wave transmitting/receiving device.

Next, the process of bending the signal conductors 51 of the above endoscope will now be described with reference to FIGS. 6 to 11. The image sensor 50 to which the one ends of the signal conductors 51 are connected is attached to the rigid portion 40, and the guide tube 53, the water feed tube 54, the air feed tube 55, the optical fiber bundles 52 and the operating wires (not shown in FIG. 6) are connected at their one ends to the rigid portion 40. Then, the signal conductors 51 are processed or bent using a jig 60.

First, the jig 60 for processing the signal conductors 51 will be described. The jig 60 has an elongated base or body 61 of a generally U-shaped cross-section, the base 61 having a pair of opposed side walls 62. The pair of side walls 62 have respective vertical portions 62a disposed parallel to each other, and respective inclined portions 62b extending respectively from the lower ends of the vertical portions 62a. The lower ends of the inclined portions 62b are interconnected. The base 61 has an upwardly-opening groove 63 which extends longitudinally from one end of the base 61 to the other end thereof.

A plurality of pairs of first and second engagement members 65 and 66 corresponding in number to the signal conductors 51 to be processed are mounted on each of the two side walls 62. More specifically, six pairs of engagement members 65 and 66 are mounted on the right side wall 62 (FIG. 6), and five pairs of engagement members 65 and 66 are mounted on the left side wall 62. The first engagement members 65 are mounted on the vertical portion 62a of the side wall 62, and are arranged in a row and spaced from one another at a predetermined pitch (that is, at equal intervals) in the longitudinal direction of the base 61. The second engagement members 66 are mounted on the inclined portion 62b of the side wall 62, and are arranged in a row and spaced from one another in the longitudinal direction of the base 61 at a pitch equal to the pitch of the first engagement members 65. Each second engagement member 66 is displaced in the longitudinal direction of the base 61 rearwardly one pitch with respect to its mating first engagement member 65. Therefore, a straight line extending between each pair of engagement members 65 and 66 is inclined with respect to the longitudinal direction of the base 61. Even pairs of engagement members 65 and 66 are mounted on the right side wall 62 (FIG. 6), and odd pairs of engagement members 65 and 66 are mounted on the left side wall 62. Therefore, the engagement members 65 and 66 on the left side wall 62 are displaced a half of the pitch from the engagement members 65 and 66 on the right side wall 62 in the longitudinal direction of the base 61.

As shown in FIG. 10, the engagement member 65 and the engagement member 66 are identical in shape to each other, and each of the engagement members 65 and 66 has a proximal portion 65a, 66a fixedly fitted in a mounting hole 62c formed through the side wall 62, a neck 65b, 66b having a diameter smaller than the diameter of the proximal portion 65a, 66a and projecting outwardly from the outer surface of the side wall 62, and a head 65c, 66c having the same diameter as the proximal portion 65a, 66a and formed on the distal end of the neck 65b, 66b. The proximal portion 65a, 66a is coaxial with the head 65c, 66c, and the neck 65b, 66b is eccentric from the proximal portion and the head. More specifically, the necks 65b and 66b of each pair of engagement members 65 and 66 are eccentric away from each other in the longitudinal direction of the base 61, as shown in FIG. 11.

The signal conductors 51 are processed or bent using the jig 60 of the above construction. As shown in FIG. 6, the jig 60 is positioned rearwardly of the rigid portion 40. The guide tube 53 is passed through the groove 63 of the jig 60. One optical fiber bundle 52 is disposed outside of the right side wall 62, and the other optical fiber bundle 52, the water feed tube 54 and the air feed tube 55 are disposed outside of the left side wall 62. Then, six out of the eleven signal conductors 51 are disposed outside of the right side wall 62 of the jig 60, and the remainder (i.e., the other five) is disposed outside of the left side wall 62. Thus, the signal conductors 51 are divided in right and left directions into generally halves.

Then, each signal conductor 51 is engaged with the neck 65b of the corresponding first engagement member 65, and is bent therearound obliquely downwardly along the outer surface of the side wall 62, and is further engaged with the neck 66b of the corresponding second engagement member 66, and is bent therearound to extend in the longitudinal direction of the jig 60. The signal conductor 51 thus processed has the front portion 51a extending from the rigid portion 40 to the first engagement member 65, the intersecting portion 51b extending from the first engagement member 65 to the second engagement member 66, and the rear portion 51c extending rearwardly from the second engagement member 66.

In this manner, all of the signal conductors 51 are bent or processed, and thereafter the signal conductors 51 are removed from the jig 60. Then, the signal conductors 51, the optical fiber bundles 52, the water feed tube 54, the air feed tube 55, the guide tube 53 and the operating wires are passed through a tube assembly (not shown) including the bending portion 30 and the insertion portion 20.

FIG. 12 shows a modified jig 60A. The jig 60 A has a base 61A of a channel-shaped cross-section defined by a pair of parallel opposed side walls 62A and a bottom wall 64A interconnecting the side walls 62A at their lower ends, the bottom wall 64A being disposed perpendicular to the side walls 62A. The two side walls 62A define, together with the bottom wall 64A, a groove 63A extending in the longitudinal direction of the base 61A. As described above for the jig 60 of FIG. 6, the plurality of pairs of engagement members 65 and 66 are mounted on each of the side walls 62A.

FIG. 13 shows another modified jig 60B which differs from the jig 60A of FIG. 12 on the following points. In this embodiment, a plurality of elongated engagement members 67 are mounted on each of the opposed side walls 62A of the base 61A. Each of the engagement members 67 is disposed perpendicular to the longitudinal direction of the base 61A, and has a neck 67b projecting outwardly from the outer surface of the side wall 62A, and a head 67c formed on the distal end of the neck 67b. The upper end of the engagement member 67 and the lower end of the engagement member 67 disposed rearwardly thereof and adjacent thereto constitute a pair of first and second engagement portions for processing one signal conductor 51.

The two side walls of the above-mentioned jigs may be curved, in which case the intersecting portion of each signal conductor is correspondingly curved.

What is claimed is:

1. A jig for processing signal conductors extending from an electric device attached to a rigid portion provided at a distal end of an endoscope, comprising:
   (a) an elongated base; and
   (b) a plurality of pairs of first and second engagement portions provided on each of opposite sides of said base, said pairs of first and second engagement portions being spaced from each other in a direction intersecting a longitudinal direction of said base, said first engagement portions being arranged substantially in a row and spaced from one another in the longitudinal direction of said base, and said second engagement portions being arranged substantially in a row and spaced from each other in the longitudinal direction of said base;
   (c) said signal conductors extending from said electric device being adapted to be divided into two groups which are disposed respectively adjacent to the opposite sides of said base, each of said signal conductors being engaged with a respective one of said pairs of said first and second engagement portions, said signal conductor being engaged with the corresponding first engagement portion to be directed toward the corresponding second engagement portion, and further engaged with said corresponding second engagement portion to extend in the longitudinal direction of said base.

2. A jig according to claim 1, in which said each pair of first and second engagement portions are disposed on a straight line inclined with respect to the longitudinal direction of said base.

3. A jig according to claim 1, in which said each pair of first and second engagement portions comprise separate projections, respectively, each of said projections having a neck and a head formed on a distal end of said neck, said head being greater in diameter than said neck.

4. A jig according to claim 1, in which a plurality of elongated projections are formed on each of the opposite sides of said base, each of said elongated projections extending in a direction intersecting the longitudinal direction of said base, and said each pair of first and second engagement portions being constituted respectively by oppositely-directed ends of any two adjacent ones of said elongated projections.

5. A jig according to claim 1, in which said base has a longitudinal groove for receiving an elongated component part extending from said rigid portion of said endoscope.

* * * * *